United States Patent
Pardue et al.

(10) Patent No.: US 6,582,661 B1
(45) Date of Patent: Jun. 24, 2003

(54) INTEGRATED LUBRICANT ANALYZER

(75) Inventors: Bradley D. Pardue, Blaine, TN (US);
Raymond E. Garvey, III, Loudon, TN (US); Anthony J. Hayzen, Knoxville, TN (US); Mark L. Granger, Knoxville, TN (US)

(73) Assignee: CSI Technology, Inc., Wilmington, DE (US)

( * ) Notice: Subject to any disclaimer, the term of this patent is extended or adjusted under 35 U.S.C. 154(b) by 363 days.

(21) Appl. No.: 09/607,665

(22) Filed: Jun. 30, 2000

(51) Int. Cl.[7] .......................... G01N 33/26; G01N 33/48
(52) U.S. Cl. .......................... 422/68.1; 422/50; 422/61; 422/62; 436/60
(58) Field of Search .................... 436/60; 73/863.21, 73/54.01, 53.01; 422/82.01, 50, 68.1

(56) References Cited

U.S. PATENT DOCUMENTS

| | | |
|---|---|---|
| 3,392,331 A | 7/1968 | Coulter |
| 3,844,160 A | 10/1974 | Yamaoka |
| 4,236,404 A | 12/1980 | Ketchum et al. |
| 4,255,166 A | 3/1981 | Gernand et al. |
| 4,257,775 A | 3/1981 | Ladov et al. |
| 4,583,396 A | 4/1986 | Hunt et al. |
| 5,095,740 A | 3/1992 | Hodgson et al. |
| 5,262,732 A | 11/1993 | Dickert et al. |
| 5,385,043 A | 1/1995 | Fitch et al. |
| 5,506,501 A | 4/1996 | Fogel et al. |
| 5,604,441 A | 2/1997 | Freese et al. |
| 5,610,706 A | 3/1997 | Carroll et al. |
| 5,614,830 A | 3/1997 | Dickert et al. |
| 5,656,767 A | 8/1997 | Garvey, III et al. |
| 5,674,401 A | 10/1997 | Dickert et al. |
| 6,023,961 A * | 2/2000 | Discenzo et al. ........... 73/54.01 |
| 6,196,057 B1 * | 3/2001 | Discenzo ..................... 73/54.01 |
| 6,286,363 B1 * | 9/2001 | Discenzo ..................... 73/53.01 |
| 6,418,799 B1 * | 7/2002 | Pardue et al. ............. 73/863.21 |

FOREIGN PATENT DOCUMENTS

| | | |
|---|---|---|
| GB | 2103 358 B | 2/1983 |
| GB | 2165650 B | 4/1986 |

OTHER PUBLICATIONS

"The Mini–Lab Concept as an Alternative to Conventional Oil Analysis" by Grahame Fogel, 1995.

* cited by examiner

Primary Examiner—Jill Warden
Assistant Examiner—Brian Sines
(74) Attorney, Agent, or Firm—Luedeka, Neely & Graham, PC

(57) ABSTRACT

An integrated lubricant analyzer apparatus. The apparatus includes a housing having a first fluid inlet port in flow communication with a chemical analysis device. A second fluid inlet port is included in the housing in flow communication with a particle analyzer. The housing also includes a third fluid inlet port in flow communication with an optical particle counting device. A syringe degassing port is attached to the housing for inverting and degassing a syringe containing a fluid sample for a particle count analysis before the fluid sample is injected into the third fluid inlet port. The apparatus includes a sample analysis sequencing procedure and a microprocessor for collection and manipulation of data from the chemical analysis device, the particle analyzer and the particle counting device. Features of the invention enable a trivector analysis of a fluid for maintaining machinery containing the fluid.

24 Claims, 9 Drawing Sheets

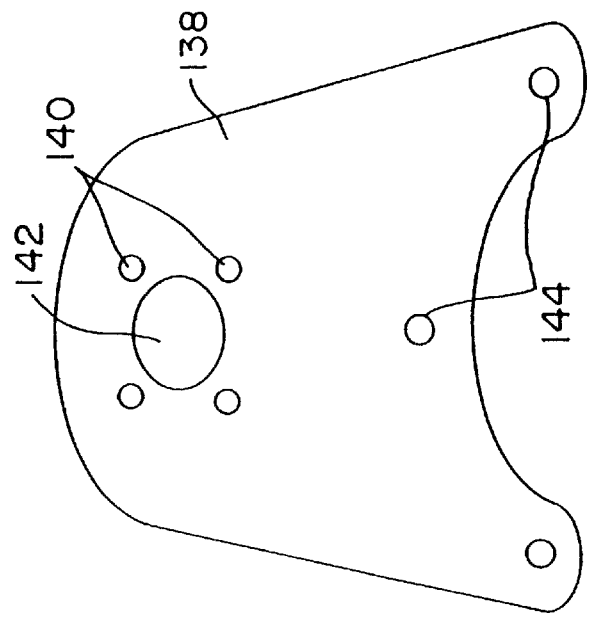
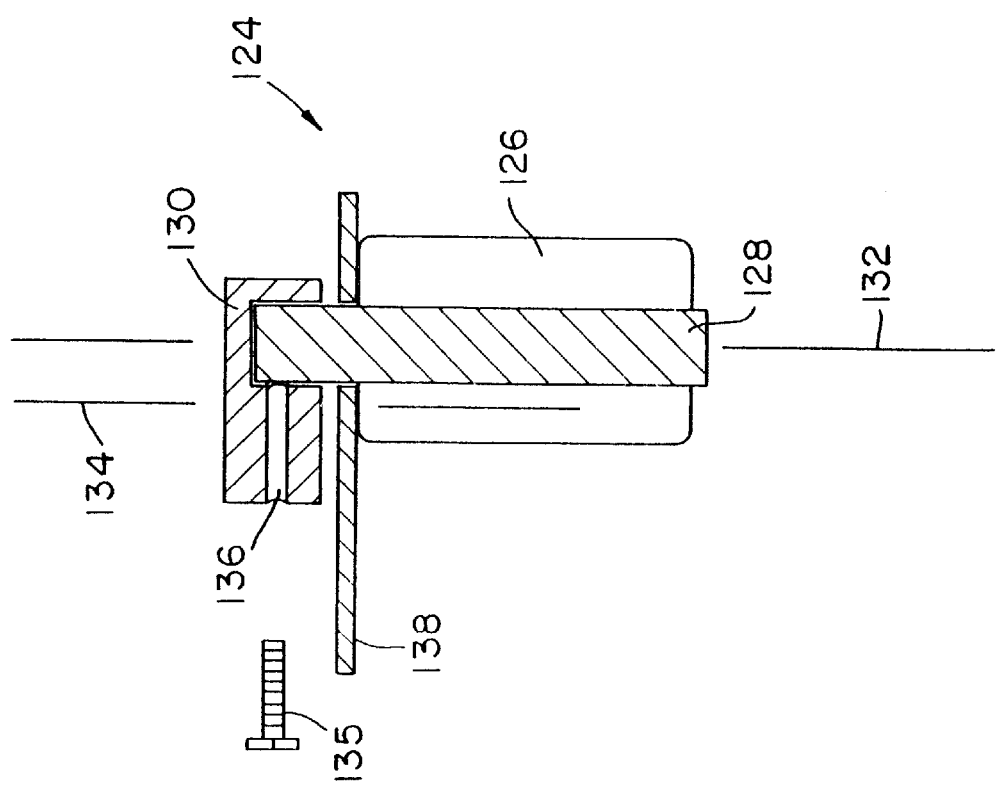

INTEGRATED LUBRICANT ANALYZER

FIELD OF THE INVENTION

The invention relates to a lubricant analyzer and in particular to an integrated lubricant analyzer which provides information about machine wear, lubricant contamination and lubricant chemistry and which provides predictive information with regard to surface degradation based on the analytical results.

BACKGROUND OF THE INVENTION

Over the life of lubricated mechanical equipment, premature failure may occur for reasons other than reaching the end of the useful life of the equipment. Such premature failures may be the result of unexpected conditions such as mechanical accidents, power failures and the like. Such unexpected conditions account for a number of the causes of equipment failure. A more dominant cause of equipment failure, is premature failure as a result of surface degradation of the lubricated surfaces of interfacing parts. Surface degradation may be the result of corrosion of the surfaces caused by moisture or other contaminants in the lubricant or by wear caused by particles or solids in contact with the surfaces of the interfacing parts. Typically, corrosion accounts for about 20% of the surface degradation-based failures of equipment. Wear is believed to account for about 50% of the surface degradation-based failures of equipment.

Although industrial lubricating fluids are normally oils, either natural or synthetic, having some degree of lubricity, this is not true in every case. Water and solvent based fluids also have wide industrial utility as coolants or flushing fluids, for example. In industrial fluid systems such as hydraulic, lubrication, fuel and metal cutting process systems, it is essential to detect and measure the concentration of particulate contaminants entrained in the fluids. High levels of certain contaminants can dramatically decrease the efficiencies and life of machinery associated with the fluids.

Various laboratory methods exist for semiquantitative analysis of particulates and solids in such industrial fluids. For example, the silting index method of determining the degree of contamination is essentially a laboratory-oriented technique which provides a semiquantitative assessment of particulate contamination in the silt size range of between approximately 0.5 to 5.0 micrometers. In essence, this known method measures the decay in the rate of fluid flow resulting from the clogging of a membrane when a contaminated fluid sample is passed therethrough. Particles having a size greater than the pore size of the membrane are retained by the filter medium membrane. The silting index method is characterized by poor repeatability because particles which are much greater in size than the silt sized pores of the membrane form a loose, open filter cake, while particles having a smaller size than the pore size, or stable gels resulting from oxidation products and polymers, tend to block the pores of the membrane in an unpredictable manner.

Another known system for determining the level of contamination in a fluid utilizes the passing of the system fluid through a filter medium until a predetermined pressure drop is achieved across the filter medium. The level of contamination in the fluid is determined by measuring the time required to reach the predetermined pressure level. This method, therefore, has several problems. First, the known method is sensitive to the pressure level of the system upstream of the sensing filter medium, thereby requiring the use of an auxiliary pump to circulate a stream of the fluid at a constant pressure. This known system, therefore, produces a contamination indication which is subject to the effects of system flow rate, system pressure differential and fluid viscosity. Correction of the results produced by this system to compensate for such effects would require substantial additional cost.

Attempts have been made to provide analytical equipment which may be used to determine the root causes of equipment failure. Such equipment has been limited to monitoring or analysis of a single parameter or characteristic of the lubricant once the most dominant cause of equipment failure has been identified. The determination of multiple properties of lubricating fluids requires multiple stand-alone instruments. There exists a need for an integrated lubricant analyzer which has the ability to monitor and predict equipment failure based on corrosion and wear with the ability to identify the primary source or sources of wear of the lubricated surfaces.

SUMMARY OF THE INVENTION

With regard to the above and other objects and advantages thereof, the invention provides an integrated lubricant analyzer apparatus. The apparatus includes a housing having a first fluid inlet port in flow communication with a chemical analysis device for chemical analysis of fluid communicated to the chemical analysis device via the first fluid inlet port. Analysis of a fluid sample inserted in the first fluid inlet port provides chemical data corresponding to chemical properties of the fluid communicated to the chemical analysis device. A second fluid inlet port is included in the housing in flow communication with a particle analyzer for providing particle identification data corresponding to particle properties of fluid communicated to the particle analyzer via the second fluid inlet port. The housing also includes a third fluid inlet port in flow communication with an optical particle counting device for providing particle count data corresponding to particle properties of fluid communicated to the particle counting device via the third inlet port. A syringe degassing port is attached to the housing for inverting and degassing a syringe containing a fluid sample for particle count analysis before the fluid sample is injected into the third fluid inlet port. An automatic sample injection device for injecting a fluid sample through the third fluid inlet port. The apparatus includes a sample analysis sequencing procedure for sequential analysis of the fluid samples. A microprocessor is contained within the housing for collection and manipulation of data from the chemical analysis device, the particle analyzer and the particle counting device for providing an output to a user indicating corrective action required based on the sample data.

In another aspect the invention provides a method for analyzing a lubricant sample for corrosive and abrasive components using the above described lubricant analysis device. According to the method, a lubricant sample to be analyzed is collected and a first portion of the sample is injected into the first fluid inlet port. A second portion of the sample is deposited in the second fluid inlet port. A third portion of the sample is degassed and injected into the third fluid inlet port. Analysis is collected on each of the samples providing chemical analysis data, particle identification data and particle count data and an output is provided by the device to a user indicating corrective action to be taken based on the data. In yet another aspect the invention provides a lubricant analyzer apparatus including a fluid inlet port for a lubricant sample, a sample syringe containing a plunger for injecting the lubricant sample into the fluid inlet port and a syringe degassing device for removing entrained and dissolved gases from the lubricant sample prior to injecting the sample into the inlet port. The degassing device is provided with a syringe adapter for connecting the syringe in an inverted orientation thereto for degassing a fluid sample in the syringe. The degassed sample is injected into the fluid inlet port at a predetermined rate using a linear motion-controlled arm attached to the syringe plunger. A particle counting device in flow communication with the fluid inlet port provides particle count data respective of particle contamination of the lubricant sample.

Yet another aspect of the invention provides an integrated lubricant analysis device which includes a housing containing at least three fluid analysis devices in electronic communication with a microprocessor for manipulation of data obtained from the fluid analysis devices. A series of light emitting diodes provide indication to a user of a predetermined analysis sequence. The analysis device includes a selector switch having positions corresponding to the predetermined analysis sequence for selecting an analysis device sample analysis and for input of data to the microprocessor, the position of the selector switch being selected by the user in response to activation of one or more of the light emitting diodes by the microprocessor.

The apparatus of the invention provides a substantially completely integrated analytical device which may be used to monitor and predict the cause or causes of equipment failure based on a trivector analysis of an oleaginous fluid. The term "trivector analysis" refers to a unique system in which the severity of changes in lubricant chemistry, machine wear and contamination is plotted on a three-spoke spider chart. This plot provides a quick overall view of the lubricant and machine so that maintenance technicians spend less time interpreting numerical data in a spreadsheet. An unique feature of the invention is that the apparatus provides integrated analysis of lubricant chemistry, machine wear and contamination in a single integrated instrument. Another unique feature of the invention is that the apparatus provides a means for obtaining a more accurate particle count than other particle count instruments as a result of a degassing apparatus and procedure included in the apparatus. It will be recognized that the term "particle", as used herein, is not intended to be limited to solid materials but also includes fluid or liquid materials which are immiscible in oil such as water droplets.

BRIEF DESCRIPTION OF THE DRAWINGS

Further features and advantages of the invention will become apparent by reference to the detailed description when considered in conjunction with the figures, which are not to scale, wherein like reference numbers indicate like elements through the several views, and wherein:

FIG. 7 is a cross-sectional view of a vibrator according to the invention;

FIG. 8 is a top plan view of a connecting bracket for a vibrator according to the invention;

DETAILED DESCRIPTION OF THE PREFERRED EMBODIMENTS

Figure 1:
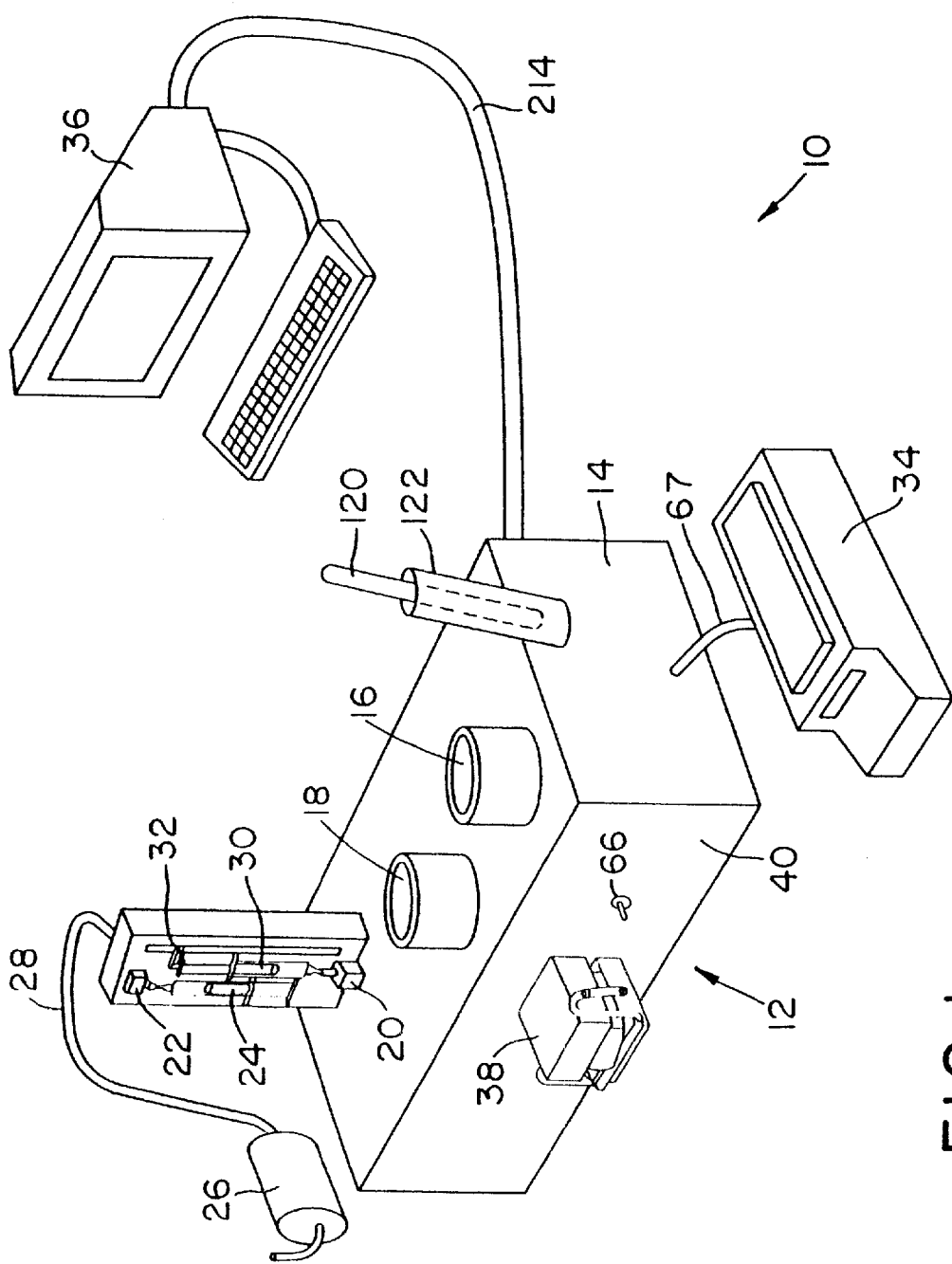
FIG. 1 is a perspective view of a lubricant analysis device according to the invention.

With reference to FIG. 1, the invention provides an integrated analytical system 10 which may be used to provide comprehensive analysis of oleaginous fluids. The key component of the system 10 is a trivector lubricant analyzer 12. The analyzer 12 is a microprocessor controlled device which includes a housing 14 having a first fluid inlet port 16 in flow communication with a chemical analysis device, described in more detail below, for chemical analysis of a fluid sample. A second fluid inlet port 18 included in the housing 14 is in flow communication with a wear debris analyzer which is described in more detail below. The housing 14 also includes a third fluid inlet port 20 in flow communication with a particle counting device as described in more detail below. The analyzer 12 is powered by an external power supply or may be adapted to include an internal power source. All calibration information may be stored in a memory module included with the microprocessor unit or in a separate memory storage device such as by means of a personal computer which is connected to the analyzer 12 through one or more communications (COM) ports.

An important feature of the invention is a sample degassing station 22 for degassing a fluid sample in a syringe 24 prior to analysis. The sample is degassed using a vacuum source such as a vacuum pump 26 connected by a conduit 28 to the degassing station 22. After the sample in syringe 24 is degassed, the syringe 24 is inverted as indicated by syringe 30 for injection of the degassed sample into the third fluid inlet port 20. It is preferred to include an automated syringe plunger control arm 32 for injection control of the sample into the third fluid inlet port 30. The degassing station 22 and control arm 32 will be described in more detail below with respect to FIG. 3.

An advantage of the degassing station 22 is that gas bubbles are removed from the sample immediately prior to analysis. This is advantageous because gas bubbles interfere with accurate particle counting when using an optical particle counter. Another advantage is that upon inverting the syringe as shown by syringe 30, any solids which may have settled in the fluid are again entrained so that a more representative sample of fluid is analyzed. The analysis is also conducted by flow downward through the analyzer 12. Analytical instruments which induce upward flow of a sample through an analyzer are less likely to achieve representative analytical results because of settling of larger particles in the sample.

The analyzer 12 is also adapted to be connected to an electronic weighing device such as electronic scale 34 and a portable computing device such as computer 36 for feedback to the user of analytical results and operational status of the analyzer 12. Additional analysis of particle size characteristics and distribution may be determined by use of a filter patch device 38 which may be attached to the housing 14 of the analyzer.

Figure 2:
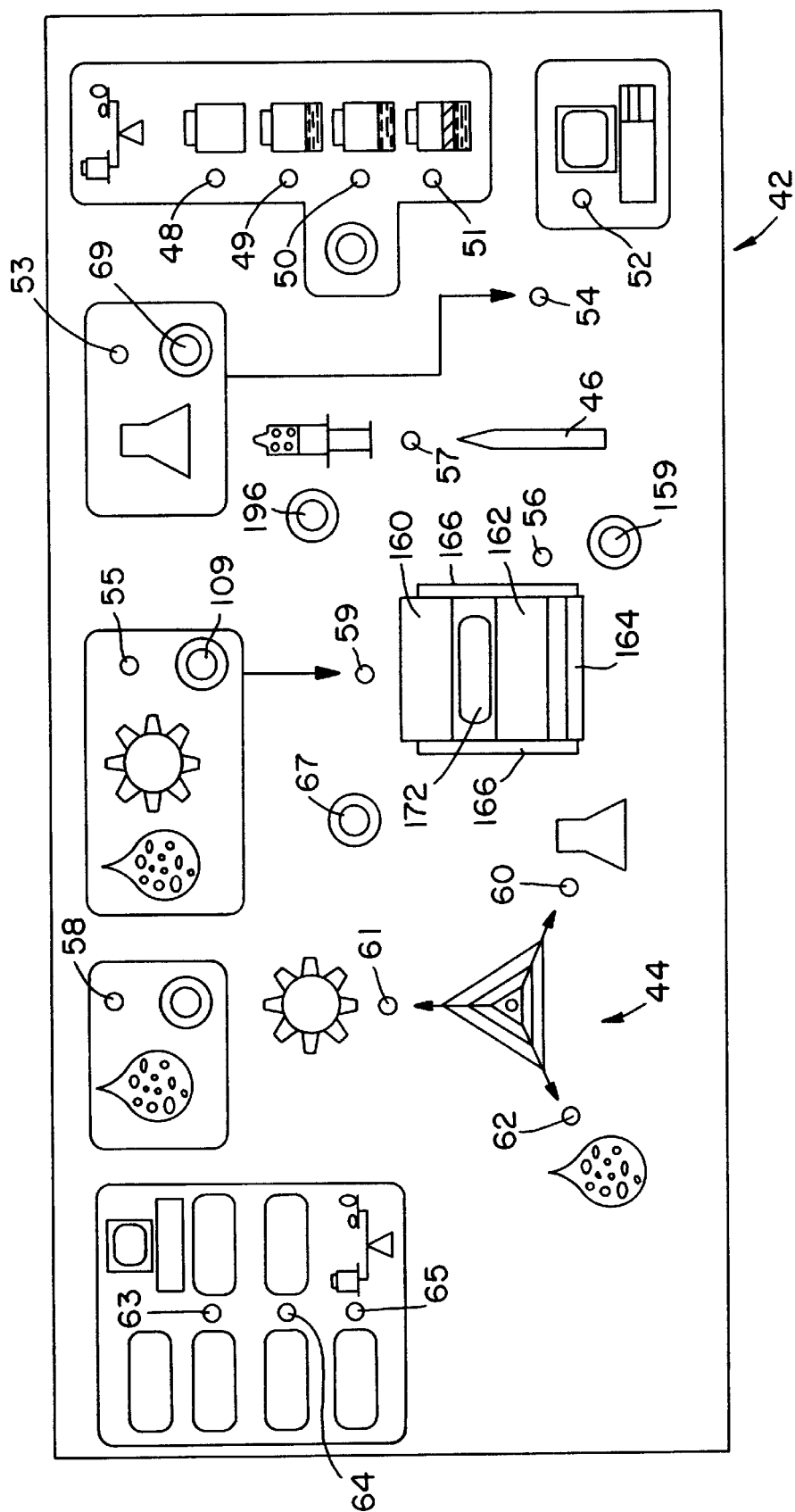
FIG. 2 is a plan drawing of a front panel containing sequencer indicators for a lubricant analysis device according to the invention.

With reference to FIG. 2, the invention also provides a user interface for carrying out a predetermined analysis sequence. The user interface is provided on the front panel 40 of the housing 14 and includes a diagram 42 representing the sequence of analysis to be performed on the lubricant samples in accordance with a trivector analysis procedure represented by logo 44. A rotatable selector switch 46 is positioned by a user in response to visual signals provided on the diagram 42 in order to provide the data for trivector analysis of an oleaginous sample.

With respect to the analysis sequence, visual and audible signals may be provided to the user to signal starting, ending or intermediate steps in the analysis process. Visual signal indicators such as light emitting diodes (LED's) 48–65 are preferably provided in the diagram 42 to provide a signal to a user as to the current state of the analysis and the next step in the analysis sequence. All of the LED's 48–65 are activated by a software program included in the microprocessor.

In the first step of the analysis, a representative lubricant sample, preferably about 50 mL is obtained from the operating lubricant in a machine. Upon energizing the analyzer with start button 66, the software activates LED 48 to indicate that a sample bottle is to be weighed prior to filling the bottle with a sample fluid to be tested to provide a tare weight. The tare weight of the sample bottle is stored in a memory device indicated by LED 52. After weighing the sample bottle, LED 49 is activated to indicate that a neat lubricant sample is to be prepared and weighed. Typically a 10 to 15 mL sample is inserted into the sample bottle and the bottle is weighed on electronic scale 34 to obtain the weight of lubricant to be analyzed. The scale 34 is electrically connected by conduit 67 to the analyzer 12 (FIG. 1) and the sample weight is also stored in a memory device as indicated by LED 52.

The initial test in the analysis sequence is a chemistry test indicated by LED 53 which is typically performed on the neat lubricant sample. The primary chemistry test is a dielectric measurement using a dielectric sensor which measures the capacitive impedance of a lubricant sample. Such a device are described for example in U.S. Pat. No. 4,471,295 to Vermeiren, U.S. Pat. No. 5,507,178 to Dam and U.S. Pat. No. 5,656,767 to Garvey III, et al., the disclosures of which is incorporated by reference as if fully set forth herein. A dielectric sensor typically includes two contact means acting as "capacitor plates" and taking the form of metal strips or pins in contact with the lubricant. A voltage signal applied the strips or pins and lubricant is compared to a reference voltage stored in memory in the microprocessor obtained from a new or uncontaminated lubricant sample. The voltage difference between the measured voltage and a reference voltage indicate the degree and/or source of contamination in the lubricant sample. If the dielectric property difference is 0.1 milliamps (ma) or more, the lubricant is unsuitably contaminated and may have corrosive properties.

Figure 3:
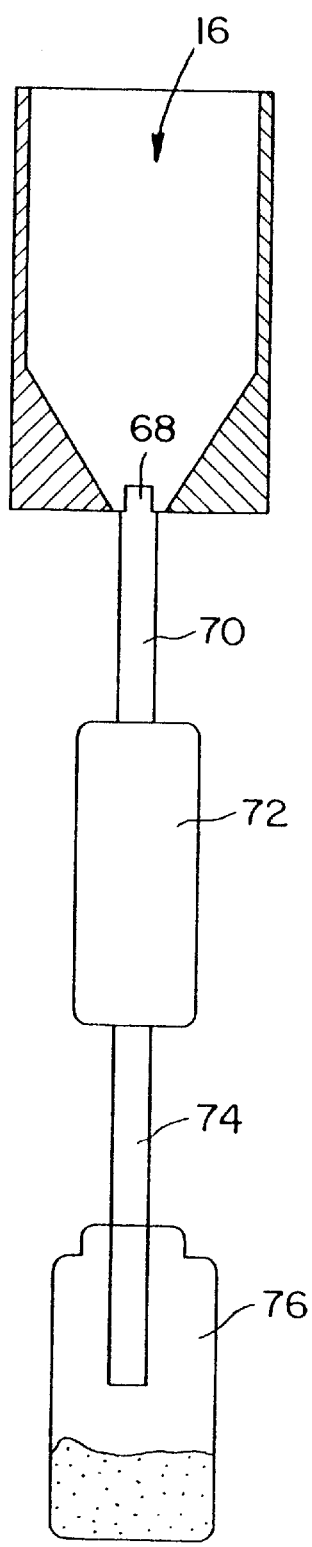
FIG. 3 is a schematic representation of a chemical analysis device according to the invention.

With reference to FIGS. 1 and 3, inlet port 16 is provided in the analyzer 12 for holding and/or injecting a sample fluid to be analyzed. The inlet port 16 preferably includes a luer fitting 68 for connection to a syringe for injecting a sample of fluid into the analyzer. Upon injection of the sample into inlet port 16, start button 69 is depressed on the panel 40. The fluid flows through an inlet conduit 70 to a dielectric sensor 72 which senses dielectric information corresponding to the dielectric properties of the fluid. The dielectric data obtained from this measurement is relayed to the microprocessor which compares dielectric properties of a fresh and/or uncontaminated sample of fluid with the measured dielectric properties of the sample fluid and stores any differences between the dielectric properties in memory indicated by LED 52.

Upon completion of the chemistry analysis, LED 57 is activated to indicate to the user to rotate selector switch 46 to LED 54 to remove the fluid from the dielectric sensor 72 through an outlet conduit 74 into a waste disposal vessel 76 or the analyzed fluid may be reintroduced to the sample bottle which initially contained the weighed sample to be analyzed. If desired, the sensor and conduits may be flushed with a solvent such as kerosene.

Figure 4:
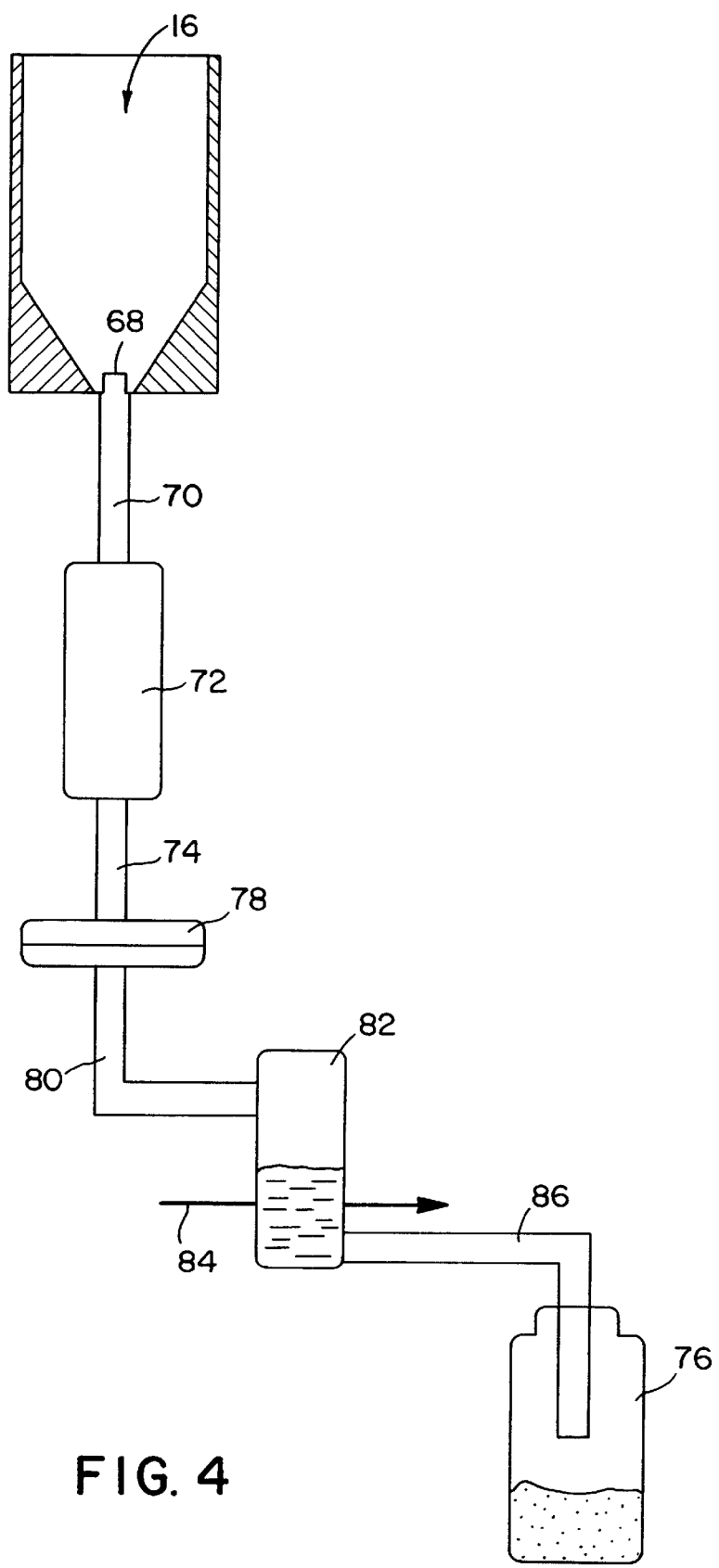
FIG. 4 is a schematic representation of an alternative chemical analysis device according to the invention.

In an alternative embodiment of the invention, additional chemical analyses may be performed on the undiluted sample. Such analyses may include one or more of viscosity and/or colorimetric properties of the fluid. Accordingly as shown in FIG. 4, the fluid may flow through outlet conduit 74 into a viscometer such as a digital viscometer 78 as described in U.S. Pat. No. 5,394,739 to Garvey, III et al., the disclosure of which is incorporated by reference as if fully set forth herein.

The fluid sample may then flow through outlet conduit 80 from the viscometer 78 into the disposal vessel 76 upon rotation of selector switch 46 to position LED 54 or to a colorimeter or optical spectrometer 82 as described in U.S. Pat. No. 5,194,910 to Kirkpatrick, Jr. et al., the disclosure of which is incorporated by reference as if fully set forth herein. As a light beam 84 of one or more wavelengths is passed through the sample, the amount of transmittance, reflectance and/or absorbance of the light beam is measured. The light transmission, reflectance and/or absorbance properties are compared to those of fresh or uncontaminated lubricants and provide an indication of the contamination level or other properties of the sample fluid.

Upon completion of the chemical analysis as indicated by activation of LED 60, rotation of the selector switch 46 to activated LED 54 induces flow of the fluid through outlet conduit 86 into the disposal vessel 76. The fluid flow through the chemistry analyzer may be induced by gravity, pressure or by applying a reduced pressure to the conduits 70, 74, 80 and/or 86. Furthermore, while a particular sequence of analysis is depicted in FIG. 4, it will be recognized that one or more of the sensors 72, 78 and 82 may be included in any order thereof. For purposes of the invention, it is preferred to included at least the dielectric sensor 72 in the analyzer 12 for determining chemical properties of the sample fluid.

When the chemistry test(s) on the lubricant sample or complete, the software will activate LED 50 to indicate the step of dilution of the lubricant sample with a compatible solvent such as kerosene (FIG. 2). Twenty-five milliliters of lubricant sample may be diluted with about 1:1 to about 100:1 parts by volume solvent to lubricant to provide a sample having the desired viscosity. A preferred dilution ratio ranges from about 1:1 to about 6:1 parts of solvent per part by weight of lubricant. Typically the sample bottle is filled with kerosene to just below the top rim of the sample bottle and the bottle containing the lubricant and kerosene are weighed to establish the dilution ratio.

LED 55 is then activated to signal the user to pour about 30 ML of diluted sample into the second fluid inlet port 18 of the analyzer 12 (FIG. 1) in order to initiate a wear debris analysis of the sample. This analysis provides an indication of the type, amount, size and shape of ferrous and non-ferrous particles in the sample so as to provide an indication of the source of the particles so that corrective action may be taken. For example, non-ferrous particles in the lubricant such as silica, boron, sodium and/or carbon or graphite particles may result in abrasive wear, metal fatigue or corrosion of lubricated parts. An unexpected increase in ferrous particles in the lubricant may be an indication of adhesion of metal parts caused by insufficient lubricant or fatigue of metal parts due to alignment or other mechanical problems.

Figure 5:
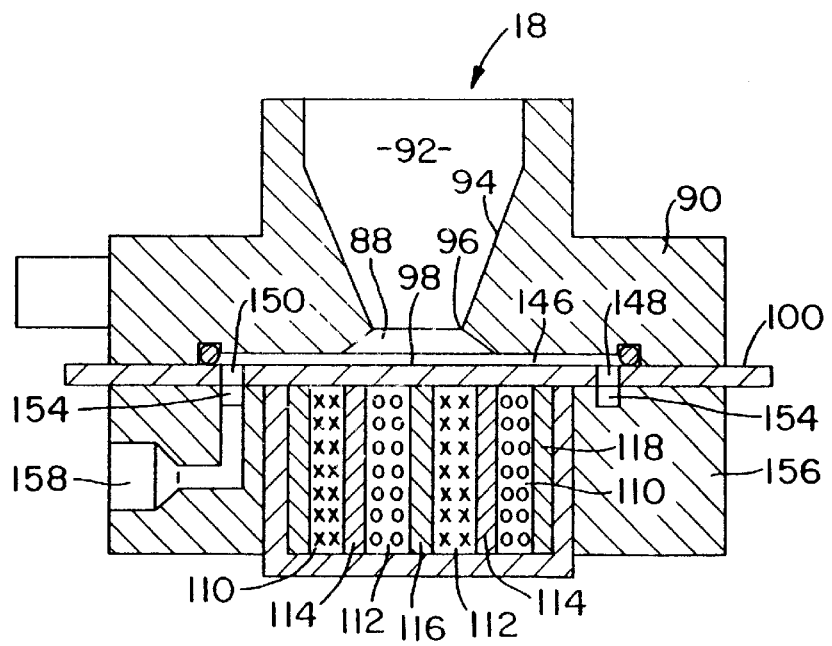
FIG. 5 is a cross-sectional view a wear debris analyzer device according to the invention.
Figure 6:
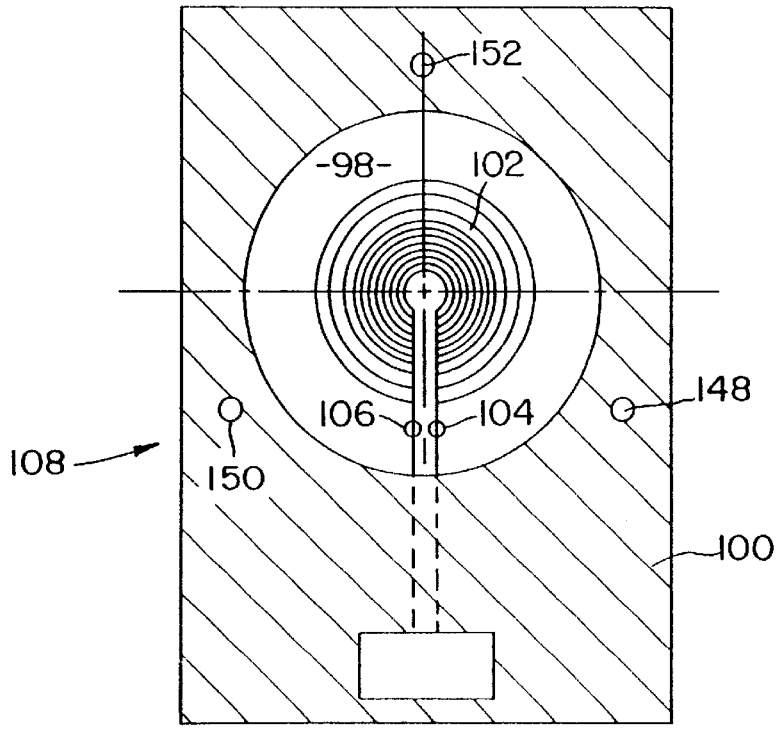
FIG. 6 is a top plan view of an insulator plate and conductive grid of a wear debris analyzer device according to the invention.

In order to conduct the wear debris analysis on a lubricant sample, the sample is conducted as by second inlet port 18 to a first chamber 88 which includes a sample chamber body 90 defining a chamber volume 92 having smooth conical walls 94 that converge into a truncated apex of a inverted cone-shaped section 96 which is axially aligned with a dielectric sensor floor 98 (FIGS. 5 and 6). The floor 98 comprises a flat plate 100 faced with a serpentine capacitor grid 102. The grid 102 is operated under control of the microprocessor in the analyzer 12 for measuring the dielectric value of a fluid that floods the grid 102. The tapered chamber body 90 as described above promotes concentration of the sample and particles in the sample on the grid 102.

The flat pate 100 is preferably made of a nonconductive substrate material such as ceramic for supporting an open grid of two conductors 104 and 106 to serve as a dielectric sensor 108. Each conductor 104 and 106 has parallel circuit extensions arced as concentric half-circles. A sampling of the fluid to be tested by the invention, wets the nonconductive plate 100 of the sensor 108 and occupies lateral space between the conductors 104 and 108. The fluid present between the concentric semi-circular conductors 104 and 108 functions as an insulating dielectric. Thus, when an electric potential difference is placed across conductors 104 and 108 upon activation of the sensor by depressing start button 109, the conductors function as capacitor plates having a capacitance which is a function of the surface area of the adjacent conductors, the distance between adjacent conductors, and the dielectric strength of the fluid interposed therebetween as related by Equation 1:

$$C = k\, E(A/d)$$

where:

C is the capacitance of the sensor k is the dielectric constant of the fluid

E is the electric potential

A is the surface area of the sensor, and d is the distance between conductors.

The dielectric strength of a fluid will change during use of the machine containing the fluid due to contamination and, frequently, due to temperature increase, thereby altering the capacitive characteristics of the sensor 108. The sensor 108 measures an increase of capacitance due to an increase in the dielectric strength of the fluid. The presence of polar oxides in the lubricant also causes an increase in the dielectric constant. Additionally, since water has a greater permittivity than oil, its presence in the oil will cause an increase in the effective dielectric constant for the sensor 108 as the water settles into the vicinity of the sensor 108.

As conductive contaminants entrained with the test sample accumulate by settling between conductors 104 and 106 over the measured test interval, the capacitance of sensor 108 decreases until it is difficult to measure. If a substantial quantity of water in the test sample accumulates on the conductors 104 and 106 of the sensor 108, an electrical short circuit between conductors 104 and 106 may result. As the capacitance decreases and the conductivity increases, changes in conductivity are more amenable to measurement than changes in capacitance since capacitance approaches zero. Thus, changes in conductivity may be analyzed in a similar manner to changes in capacitance as described below. Such characteristic changes in capacitance and/or conductivity indicative of changes in lubricant quality are a basic operating principle of the present invention.

Changes in the effective dielectric constant may also result from temperature variation. However, a number of strategies may be utilized to compensate for such changes over wide operational ranges. One such compensation technique is to establish a comparative reference sensor exposed to a control fluid. Another technique includes archiving respective capacitance values corresponding to various temperatures for fresh fluid, measuring the operating fluid temperature, and comparing the operating fluid capacitance value to the archived value at the corresponding temperature. Of course, determining and archiving a dielectric constant value or other such parameter rather than the capacitance value would provide similar results.

A wide range of fabrication parameters are suitable for the dielectric sensor 108 components depending upon the particular application. One such combination uses a sensor 108, such as the sensor having a floor, such as floor 98, beneath the inverted cone-shaped section 96 with an effective diameter of about one inch. The conductors 104 and 106 preferably have a wire diameter of about 250 microns and are spaced apart by a distance of about 250 microns. A preferred dielectric sensor 108 having these physical parameters has a nominal air capacitance (i.e. not immersed in fluid) of about 30 picofarads. When designed for continuous operation in harsh environments of solvents and high temperatures, inorganic materials such as aluminum ceramic should be considered for fabrication of the conductor substrate.

As set forth above, the sensor grid 102 is preferably charged by an oscillator circuit via conductors 104 and 106 using a monostable multivibrator to generate an output signal at a frequency corresponding to the capacitance of the sensor 108. This variable frequency output signal is transmitted to control logic in the microprocessor, which may be realized using any of a number of processing strategies without departing from the spirit or scope of the present invention. Depending upon the design parameters of the particular application, including design costs, production volume, and computational requirements, control logic may be implemented in hardware, software, or a combination thereof.

Beneath the plate 100 are a pair of magnets, at least one of which is an electromagnet having electrical connections for reversing the field polarity. In a preferred embodiment, both magnets are electromagnets represented by outer windings 110 and inner windings 112 around concentric cores such as intermediate core 114 and inner core 116 (FIG. 5). Inner core 116 is preferably a ferrite rod and the intermediate core 116 is preferably comprised of a ferrite cylinder. An outer casement 118 preferably also made of ferrite concentrically surrounds the intermediate cylinder core 116. Preferably, all of the electromagnet elements are electrically insulated and sealed together by a non-conductive potting compound to form a single integrated unit. It will be understood that although the presently preferred embodiment of the invention specifies a radially concentric, dual coil electromagnet, other configurations such as three or more radially concentric coils may be used.

During the wear test procedure, a fluid sample is placed in direct, wetting contact with the sensor grid 102 of the dielectric sensor 108. In this state, the inner windings 112 are activated to generate a flux field with respect to the inner core in the fluid sample enclosed by the chamber body 90. If ferrous or other magnetic particles are present within the fluid sample, such particles will be attracted to the wetted face of sensing grid 102. An accumulation of such magnetically responsive particles on sensor 108 increases the capacitance in accordance with Equation 1.

The intermediate core 114 may also be activated to generate magnetic flux fields in the fluid which may be same or opposite to the flux field generated by activation of the windings 112 for the inner core 116. The polarities of one or both of the electromagnets may also be changed to provide alternate flux fields in the fluid sample. In another embodiment, alternate activation of the inner and intermediate cores may be conducted to sweep magnetic particles onto or off of the grid 102 as the capacitance of the fluid is measured. By a selective switching of the inner and intermediate cores 112 and 114, magnetically responsive particles carried by the fluid are attracted to sensor grid 102 and are caused to positionally fluctuate in characteristic patterns distinctive to their size and shape.

While the tapered chamber body 90 preferably promotes concentration of the sample and particles in the sample on the grid 102, other means for concentrating the sample and particles on the grid 102 may be used alone or in combination with the tapered chamber body 90. For example, diluting a lubricant sample and/or vibrating a lubricant sample may promote settling of particles on the grid 102. Hence, sweeping of the magnetic particles in the sample onto or off of the grid 102 may be conducted when the particles are concentrated on the grid 192 by means other than the tapered chamber body 90.

Operation of the dielectric sensor 108 of the present invention provides similar results as those provided by U.S. Pat. No. 5,262,732 to A. D. Dickert et al using alternative apparatus and methods. The several test sequences and algorithms disclosed by Dickert et al are incorporated by reference as directly applicable to the present invention as if fully set forth herein. The dual-winding electromagnet configuration of this invention can be a direct substitution for the electromagnet plus permanent magnet configuration disclosed by Dickert et al, accordingly, all of the computational indices disclosed therein are equally adaptable to the present invention. Such indices include the Corrosion Index, Contaminant Index, Ferrous Index, OILLIFE Index, and Large Contaminant Indication. The present invention provides for similar measurements to be obtained from a stagnant lubricant sample in a manner similar to that disclosed by Dickert et al.

In another alternative embodiment, a permanent magnet wand 120 may be attached to the analyzer 12 by means of a wand holder 122 (FIG. 1). The wand 120 may be inserted in inlet ports 16 and 18 to remove magnetic particles from a fluid before or after conducting one or more tests on the fluid. The wand 120 is particularly useful with the wear test conducted using dielectric sensor 108 as described above.

In another alternative embodiment, the flat plate 100 of the sensor 108 may be vibrated or the fluid in chamber volume 92 may be agitated to promote settling of particles in the fluid being tested. In a preferred embodiment a vibrator 124 is attached to the body or plate 100 to promote settling of particles present in the fluid on the grid 102. With reference to FIGS. 7 and 8, the vibrator 124 may consist of a motor 126 powering a rotating shaft 128 to which is attached a weighted cylindrical body 130. The body 130 is attached to the shaft 128 so that axis 132 of the shaft 128 and axis 134 of the cylindrical body 130 are offset from one another to provide vibrational oscillations when the shaft 128 and cylindrical body 130 are rotated. The cylindrical body 130 may be fixedly attached to the shaft 128 as by means of a set screw 135 inserted in a threaded aperture 136 or by any other suitable structure for mechanical fastening thereof.

The vibrator 124 may be attached to the body 90 or plate 100 by means of an attachment plate 138 shown in detail in FIG. 8. The attachment plate 138 contains apertures 140 for fasteners such as screws or bolts for attaching the plate 138 to the motor 126 by inserting the shaft 128 of motor 126 through motor aperture 142. The plate 138 may then be attached to the chamber body 90 or preferably plate 100 by inserting fasteners such as screws or bolts through bolt hole apertures 144 in plate 138. Other means, such as welding or adhesives may be used to attach the plate 138 to the chamber body 90 or plate 100 and to attach the motor 126 to the plate 138.

It has been found, quite surprisingly, that the vibrator 124 promotes rapid settling of particles in the order of about 1.5 to about 2 times faster than without the vibrator. Accordingly, more debris settles on the sensor grip 102 per unit area providing maximum sensitivity particularly for fluids containing non-ferrous particles.

Upon completion of the wear debris analysis test using the dielectric sensor 108 described above as indicated by LED 61, LED 56 is activated to indicate that selector switch 46 is to be rotated to LED 61 so that the liquid on plate 100 located in the space 146 between the plate 100 and the chamber body 90 is caused to flow through apertures 148, 150 and 152 in plate 100 and into an annular recessed area 154 in lower body 156 (FIGS. 5 and 6). The fluids then flows from the annular recessed area 154 through an outlet aperture 158. From the outlet aperture 158, the liquid may flow to a disposal vessel such as the disposal vessel 76 (FIG. 3).

In another alternative embodiment, a definitive particle size and/or count of ferrous and/or non-ferrous particles may be obtained by use of the filter patch making device 38 (FIG. 1). Activation of LED 59 indicates the selection of the particle size and/or count test. The filter patch device 38 may be connected in fluid flow communication with the outlet aperture 158 of the lower body 156 and includes a two part body consisting of an upper block portion 160 and a lower block portion 162. The lower block portion 162 is movable vertically away from the upper block portion 160 by means of a rotatable handle 164 and linkages 166 and 168. Rotation of the handle 164 forward and upwards causes the lower block portion 162 to recede from the upper block portion 160 along guide rails 170 in order to permit the insertion of a filter patch holder 172 therebetween.

Figure 10:
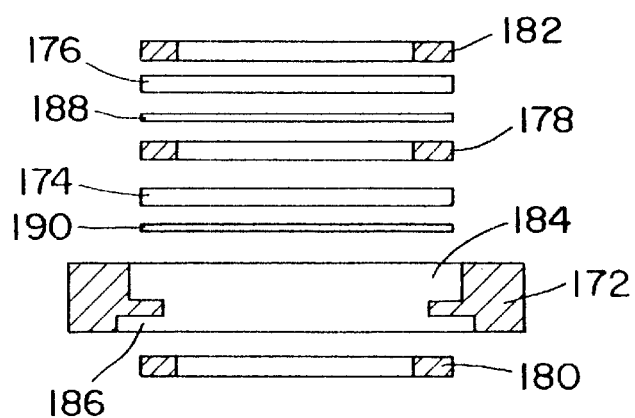
FIG. 10 is a cross-sectional view exploded view of a filter patch holder and filtering elements according to the invention.

The filter patch holder 172 is a cylindrical body which is adapted for holding one or more filter media 174 and/or 176 therein for flow of liquid therethrough (FIG. 10). Elastomeric o-rings or gaskets 178, 180 and 182 are preferably inserted in annular recess areas 1 84 and 186 to seal between the filter patch holder 172 and upper and lower body portions 160 and 162. The thickness of sealing member 102 preferably ranges from about to about 2 to about 3 millimeters and the diameter thereof preferably ranges from about 20 to about 60 millimeters. While it is preferable to position the sealing members 178, 180 and 182 within the recessed areas 184 and 186, they may also be placed elsewhere according to the defined function thereof, namely, forming seals between the holder 172 and the upper and lower body portions 160 and 162.

Preferred filter media 174 and 176 include, glass fiber, polymeric, paper or cellulosic filter paper having a wide range of pore size openings or particle size retention. In this regard it is particularly preferred to use filter media 176 having a pore size ranging from about 5 to about 30 microns, preferably from about 6 to 10 microns and filter media 174 having a pore size ranging from about 0.5 to about 20 microns, preferably from about 1 to about 5 microns.

Because the filter media 174 and 176 are typically relatively thin and flexible it is preferred to support the filter media with support screens 188 and 190. The support screens 188 and 190 may be made of a variety of thin relatively rigid materials having a mesh size ranging from about 50 microns to about 50 millimeters. Materials for the support screens 188 and 190 include metals, plastics, fiberglass and the like. Particularly preferred support screens 188 and 190 are stainless steel screens having a thickness ranging from about 5 to about 15 mils and having openings therethrough ranging from about 50 to about 60 mils in diameter.

Fluid may be caused to flow from the chamber volume 92 through the outlet conduit 158 and through the filter patch making apparatus 38 containing filter media 174 and 176 by gravity or preferably by applying a reduced or subatmospheric pressure to the fluid flow path by connecting a vacuum pump to an outlet port on the lower body portion 162. If a vacuum pump is used, it is preferred to use a pump which has a flow volume of at least about 10 scfm in order to draw the sample through the apparatus 38 in a relatively short period of time. Typically, the entire fluid sample is preferably drawn through the filter media in no more than about 120 seconds.

Once a predetermined amount of fluid has been drawn through the filter media, the filter media 90 and 92 may be rinsed with water or a solvent to remove traces of the fluid from the media. The media holder 30 containing the filter patch samples is then removed from between the inlet and outlet housings 26 and 28 by rotating handle 42 so that outlet housing 28 moves vertically away from inlet housing 26 along slide rods 52 and 54 (FIG. 1) as shown in FIG. 8. The filter media 90 and 92 containing captured particulate from the fluid may be separated from the sealing members 98 and 100 and support screens 94 and 96 (FIG. 6) and dried. The amount and size distribution of particles captured by the filter media 90 and 92 may be determined for a fixed volume of fluid by any conventional optical or visual techniques.

Figure 9:
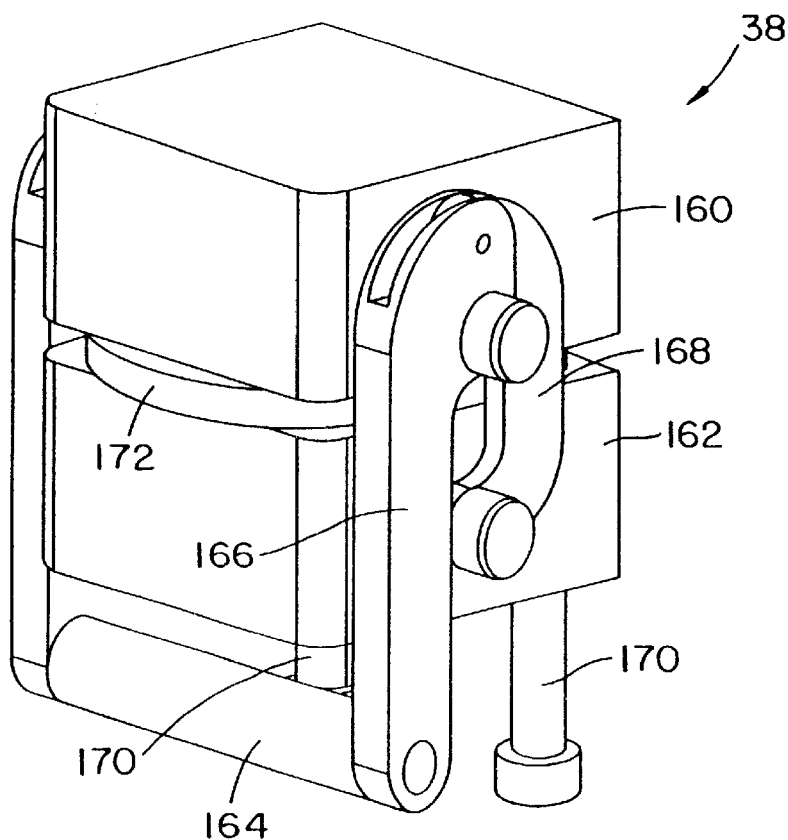
FIG. 9 is a perspective view of a filter patch making apparatus according to the invention.

As shown in FIG. 8, as the handle 42 is rotated in a clockwise direction, the outlet hosing 28 moves vertically downward along slide rod 52. As the housing 28 moves downward, the conduit 88 connected to the outlet port 68 of the housing 28 also moves downward. In order to permit the conduit 88 to moved, it is preferred that the vertical frame member 24 contain a slotted opening 120 (FIG. 9) for movement therein of conduit 88 during rotation of handle 42. Circular slot 122 in frame member 24 provides an opening for conduit 86 attached to outlet port 85 of reservoir 82.

The device as described above may be used to make a single filter patch sample or to make two filter patch samples essentially simultaneously thereby reducing the time required to prepare multiple samples having a different range of particulate retention. In this regard it is preferred to use a large pore filter paper 90 in the upper position of the filter media stack (FIG. 6) and a smaller pore filter paper 92 in the lower position of the filter media stack. This arrangement provides a means for more effective flow through the filter media so that the time required to prepare the filter patch samples is minimized.

Upon capturing particles on filter media 174 and 176, the filter media holder 172 may be removed from the filter patch making apparatus 38 and the particles captured by the filter media 174 and 176 are counted and/or identified. Methods for determining the identity, concentration and particle size distribution of particulate or contaminants in a fluid include preparing standard filter patch samples containing known particulates of known size distribution and/or concentration and comparing the standards to filter patch samples made from a fluid to be analyzed. The comparison of the filter patch samples made using apparatus 38 and standard filter patch samples may be made with the unaided eye, by use of a microscope, microscopic comparison with standard photographs or by using electronic image analysis techniques. Filter patch samples made according to the invention may also be compared by use of a weighing balance, an x-ray fluorescence spectroscopy device, magnetometer device, Hall effect flux analyzer, atomic emission spectrometer, or other devices suitable for analysis of different types of particulate material. In addition, the particulates on the filter patch samples may be re-suspended in a solution and the solution passed through an in-line optical contamination meter or the re-suspended particles may be chemically treated or reacted with solvents or other chemical reagents.

A particularly preferred use of the device according to the invention is to determine the quantity and/or size distribution of ferrous particles in a fluid sample. One method for determining such particle size and concentration is to first isolate the ferrous particles from the fluid sample such as by stirring the sample in the chamber volume 92 with magnetic wand 120 to remove the ferrous particles from the fluid before filtering the fluid sample through the filter media 174 and 176. The remaining fluid and particles are then filtered through the media as described above and the particles' concentration, size distribution and identity may determined as by a variety of techniques including the methods set forth in U.S. Pat. No. 4,047,814 to Westcott.

The ferrous particles attached to the magnetic wand 120 are then reslurried in an appropriate fluid and placed in the chamber volume 92 for filtering through fresh filter media 174 and/or 176 in filter patch making apparatus. The resulting filter patches may be analyzed by well known techniques to determine the size distribution and concentration of ferrous particles which were in the original fluid sample. The filter patch making apparatus 38 is available from Computational Systems, Inc. of Knoxville, Tenn. under the trade name WEAR DEBRIS PATCH MAKER, Model 51 WD.

Most wear particles in a lubricant result from three root causes: adhesive wear, abrasive wear, or metal fatigue. Adhesive wear is that which results from sliding, scuffing, or rubbing contact between surfaces. Sliding type adhesive wear is common and quite normal wear which occurs in most applications. Scuffing and rubbing contact typically result from a component or lubrication failure and are, therefore, not normal. Normal adhesive wear generates very small (0.1 to 5 microns) wear particles as high spots of components in sliding engagement are sheared down. Abnormal adhesion (resulting in scuffing or rubbing) may generate much larger particles.

Abrasive wear is the cutting action typically caused by hard particles gouging out relatively long strips (ranging between ten and several hundred microns) of metal which are sometimes curled. Sand or metal wear particles are frequently the cause of abrasive wear. Abrasive wear particles are eventually broken into smaller particles as they are acted upon by various contacting machinery components.

Metal fatigue (also called "high cycle fatigue") occurs when a metallic component fails due to repeated cyclic loading. This is a common failure mode for various machine components such as gear teeth and roller element bearings which are utilized in a number of diverse industrial and commercial applications. Fatigue particles tend to be relatively large (10 to 20 microns) having a parallelepiped or a spherical shape. The presence of spherical particles usually is particularly indicative of fatigue failure. These particles are generated when sub-surface cracks allow a portion of material to break free. When the surface-connected cracks join and produce a parallelepiped surface particle, the sub-surface spherical particles are also released.

By differentially capturing ferrous and nonferrous wear particles and characterizing their size and/or concentration, the present invention improves the efficiency of diagnosis and appropriate repairs prior to a system failure. A careful examination of the quantity and character of the particles provides valuable insight into their source. Maintenance and operations personnel may then pursue the correct follow-up actions. For instance, after detecting abrasive wear particles in a machine, the lubricant and filter should be changed. Seals and air filters should be inspected to determine how sand or dirt might be getting into the lubrication system. Other such appropriate diagnostic and corrective actions can be likewise pursued upon detection of any of the other types of wear particles.

Upon completion of the wear debris analysis, a user then rotates selector switch 46 to LED 56 to purge and clean the wear debris analyzer and/or filter patch making apparatus 38. When no filter patch sample is to be made, the filter patch making apparatus 38 contains no filter media 174 and/or 176 and thus the sample flows directly out of the wear debris analyzer into the disposal bottle such as bottle 76.

Next, LED 58 is activated to indicate to the user that a particle counting test is to be conducted on the fluid sample. In order to conduct the particle counting test, the remaining fluid from the initial sample is diluted with kerosene and/or 10 mL of a masking fluid such as a mixture of toluene/isopropanol as indicated by LED 51. The sample is then vigorously shaken and about 30 mL of sample are removed from the sample bottle using syringe 24.

In order to accurately count particles in the fluid sample, it has been found that water and gas bubbles should be excluded from the sample before the sample fluid flows through an optical particle counter. Gas bubbles and water interfere with conducting an accurate count of the suspended particles in a fluid sample.

Another problem with optical particle counting which this invention solves is that of obtaining a representative sample of fluid. As the fluid is diluted, larger particles tend to settle to the bottom of the sample bottle and may not flow through the particle counter. Accordingly, analysis devices which induct a fluid sample upwards through a particle counter tend to be less accurate than the particle counter according to the invention.

Figure 11:
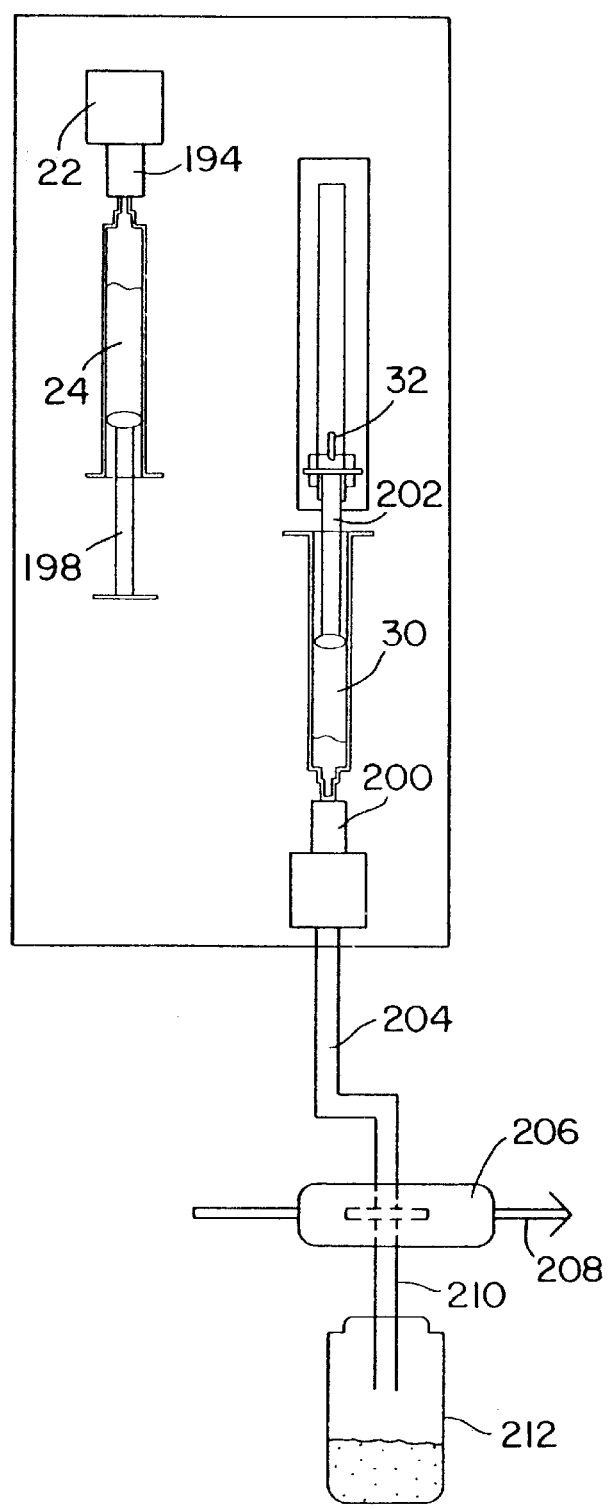
FIG. 11 is schematic representation of a fluid sample preparation and particle counting device according to the invention.

With reference to FIGS. 1 and 11, the analyzer 12 according to the invention includes a degassing station 22 containing a luer tip connector 194 for connection to a syringe 24. The syringe contains the fluid sample to be analyzed and as a first step in the particle counting process, the syringe 24 is inverted and attached to luer connector 194 as seen in the left half of FIG. 11. Activation of LED 57 indicates that a sample is to be degassed before conducting the particle counting test. A reduced pressure is then applied to the syringe 24 by vacuum pump 26 to induce flow of gas bubbles out of the fluid sample. Start button 196 is then depressed by a user to activate the vacuum pump 26 when syringe 24 is connected to the degassing station 22.

After degassing the sample fluid, the syringe 24 is disconnected from degassing station 22 and a plunger 198 of the syringe 24 is squeezed by the user to remove any air pocket which may remain above the fluid sample in the syringe 24. The syringe 24 is then rotated 180 degrees as indicated by syringe 30 and is connected to a luer connector 200 and a plunger control arm 32 for moving plunger 202 at a controlled predetermined rate for injection of the sample through conduit 204 and optical particle counter 206. Arrow 208 represents a light beam which is caused to travel through the sample in the particle counter 206 to provide absorbance, transmittance and/or reflectance characteristics of the sample which are calibrated to provide a count of the number of particles in the fluid sample. A preferred particle counter 206 is a MET ONE laser sensor Model LB 1020 available from Met One Instruments, Inc. of Grants Pass, Oreg. After flowing through particle counter 206, the fluid flows through an outlet conduit 210 into a collection vessel 212. Completion of the particle counting test is indicated by LED 62 adjacent logo 44 on diagram 42 (FIG. 2).

Figure 12:
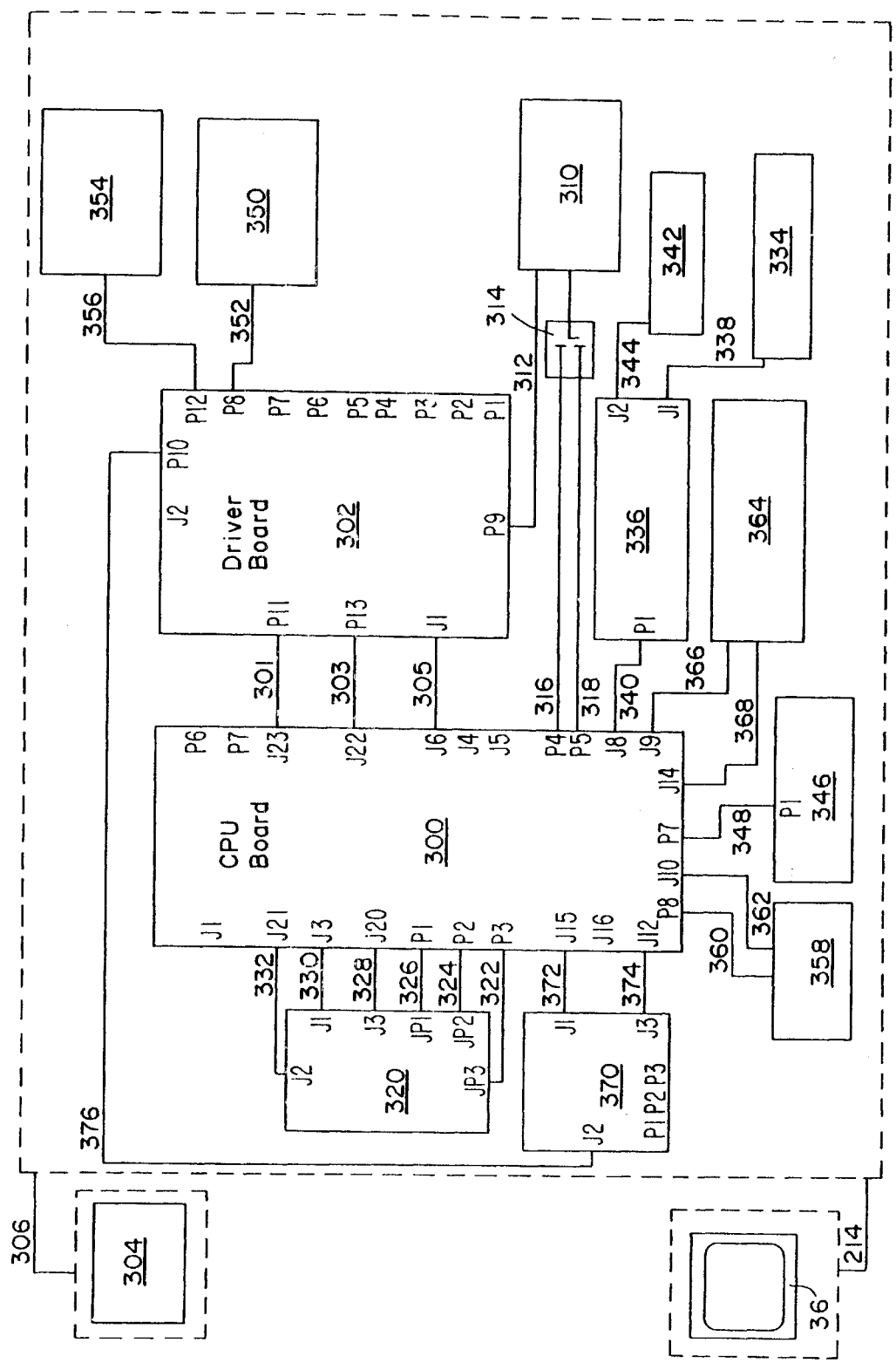
FIG. 12 is an electrical schematic drawing of the components of a lubricant analyzer device according to the invention.

With reference now to FIGS. 1 and 12, the analyzer 12 includes a main CPU board 300 adapted to include a microcontroller, such as Motorola 68HC11 available from Motorola, Inc. Semiconductor Products Sector of Austin, Tex. and associated memory devices. The construction of the main CPU board and the selection of appropriate memory devices will be apparent to one of ordinary skill in the art having the benefit of this disclosure. The analytical devices described above are attached to the CPU board 300 or to a driver board 302 which is in electrical communication with the microcontroller via the CPU board 300 via electrical connections 301, 303 and 305. The entire system is powered by a direct current power supply 304, preferably a 15 volt DC power supply. The power supply 304 may be disposed in the housing 14 or external thereto. The power supply 304 is connected to the CPU board 300 and/or driver board 302 via power conduit 306.

Upon activation of power switch 66, a stepper motor 310 is activated via driver board 302 and electrical conduit 312. Stepper motor 310 activates a sequencing switch 314 which provides power to the LED's on front panel 40 via electrical conduits 316 and 318 which are in electrical communication with the CPU board 300 and a front panel LED board 320. The activated LED's indicate the current step of the procedure as defined by a predetermined analytical sequence in response to the position of selector switch 46 (FIG. 2). The front panel LED board 320 is electrically connected to the CPU board 300 via electrical conduits 322, 324, 326, 328, 330 and 332.

Accordingly, activation of LED 53 indicates the use of neat dielectric sensor 334 which is in electrical communication with neat dielectric sensor board 336 via electrical conduit 338. The neat dielectric sensor board 336 is also in electrical communication with CPU board 300 via conduit 340. Accordingly, the neat dielectric properties of a sample are relayed to the memory on CPU board 300 for later use. The temperature of the neat sample is provided by a thermocouple probe 342 which is also electrically connected to dielectric sensor board 336 via electrical conduit 344.

During the wear debris analysis, a sample is introduced into sample chamber body 90 (FIG. 5) which contains a grid dielectric sensor board 346 providing dielectric sensor 108 which is in electrical communication with CPU board 300 via electrical conduit 348. As set forth above, it may be desirable to vibrate the fluid chamber body 90 in order to promote settling of particles present in the fluid. In this case a vibrator 350 attached adjacent chamber body 90 may be activated by driver board 302 via electrical conduit 352. As a component of the wear debris analysis, a magnetic flux field may be generated during the analysis by activating a dual coil electromagnet 354 by means of driver board 302 and electrical conduit 356.

As set forth above, a definitive particle size and/or count of ferrous and/or non-ferrous particles may be obtained by use of the filter patch making device 38. Activation of LED 59 on filter LED board 358 is provided by stepper motor 310 upon completion of the wear debris analysis test. LED board 358 is in electrical communication with CPU board 300 by means of electrical conduits 360 and 362.

Flow through particle counting is also provided by the analyzer 12. Flow through particle counting is conducted in the particle counting test using the particle counter 206 containing a laser particle sensor 364 which is connected to CPU board 300 via electrical conduits 366 and 368.

Once all of the analytical tests are complete and the data is stored in a memory, the data is analyzed either by a microcomputer chip on CPU board 300 or in a separate computing device. In a preferred embodiment, the data is collected and conducted via a COMM port board 370 via a serial cable 214 to a personal computer 36. The COMM port board 370 is in electrical communication with the CPU board 300 via electrical conduits 372 and 374 and driver board 302 via conduit 376.

Key features of the apparatus of the invention is the incorporation of degassing the fluid sample and inverting the syringe after degassing to inject the fluid sample substantially vertically downward at a controlled rate through the particle analyzer 208. It has been found that such a procedure not only provides representative and substantially reproducible results, but that it avoids the problem associated with settling of large particles in the sample fluid. While injecting a fluid sample vertically downward into a particle count analyzer is an improvement over analyzers which conduct the sample fluid upwards through a particle counter, additional accuracy is obtained by degassing the sample according to the method described above before obtaining a particle count analysis.

As set forth above, each of the analysis of chemistry, wear debris and particle count are integrated into a single analyzer 12 and the data obtained from one or more of the analyses are collected and processed as indicated by activation of LED 52 to provide a trivector analysis of the fluid indicated by logo 44 on diagram 42. The data collected from the analyzer 12 is preferably conducted to a personal computer 36 via connecting electrical conduit 214 which is a serial cable having a nine pin connector for connection to a COM port on the personal computer 36. In the alternative, the microprocessor in analyzer 12 may include a data storage device or memory for storing data for later transfer to a personal computer 36.

With reference now to FIG. 12, the housing includes a microcontroller attached to a CPU board 300. Various of the analytical instruments described above are attached to the CPU board 300 or to a driver board 310.

While the invention has been described in detail, it is to be expressly understood that various changes of form, design or arrangement may be made to the invention by those skilled in the relevant art without departing from the spirit and scope of the invention. Therefore, the above mentioned description is to be considered exemplary, rather than limiting, and the scope of the invention is defined by the following claims.

What is claimed is:

1. An integrated lubricant analyzer apparatus comprising:

a housing having a first fluid inlet port in flow communication with a chemical analysis device for chemical analysis of fluid communicated to the chemical analysis device via the first fluid inlet port, the analysis providing chemical data corresponding to chemical properties of the fluid communicated to the chemical analysis device, a second fluid inlet port in the housing in flow communication with a particle analyzer for providing particle identification data corresponding to particle properties of fluid communicated to the particle analyzer via the second fluid inlet port, third fluid inlet port in the housing in flow communication with an optical particle counting device for providing particle count data corresponding to particle properties of fluid communicated to the particle counting device via the third inlet port, a syringe degassing port attached to the housing for inverting and degassing a syringe containing a fluid sample for particle count analysis before the fluid sample is injected into the third fluid inlet port, an automatic sample injection device for injecting a fluid sample through the third fluid inlet port, and a microprocessor contained within the housing for collection and manipulation of data from the chemical analysis device, the particle analyzer and the particle counting device for providing an output to a user indicating corrective action required based on the sample data.

2. The lubricant analyzer of claim 1 further comprising a sample weighing device for input of lubricant sample weight to the computing device.

3. The lubricant analyzer of claim 1 further comprising a vacuum pump in flow communication with the syringe degassing port for degassing a lubricant sample.

4. The lubricant analyzer of claim 1 further comprising a panel on the housing containing an analysis sequencing procedure wherein the analysis sequencing procedure is indicated by a graphic and light display on the panel of the housing.

5. The lubricant analyzer of claim 1 wherein the chemical analysis device comprises a dielectric sensor and a sensor selected from a viscometer, a colorimeter and a combination of viscometer and calorimeter.

6. The lubricant analyzer of claim 1 wherein the third fluid inlet port is disposed on the housing so as to inject a lubricant sample for analysis vertically downward through the third fluid inlet port.

7. The lubricant analyzer of claim 1 wherein the automatic sample injection device comprises a linear motion-controlled arm for attachment to a syringe plunger.

8. The lubricant analyzer of claim 1 wherein the particle analyzer comprises a dual coil electromagnetic sensor.

9. The lubricant analyzer of claim 8 wherein the second fluid inlet port comprises a tapered cylindrical inlet port.

10. The lubricant analyzer of claim 8 further comprising a vibrator attached to the second fluid inlet port.

11. The lubricant analyzer of claim 1 further comprising a filter patch device attached to the housing in flow communication with the particle analyzer for visual determination of particle size distribution.

12. The lubricant analyzer of claim 1 further comprising a permanent magnet wand and a wand holder attached to the housing for metallic particle analysis.

13. A method for analyzing a lubricant sample for corrosive and abrasive components which comprises, providing a lubricant analysis device containing a housing having a first fluid inlet port in flow communication with a chemical analysis device for providing chemical analysis data of a lubricant sample, a second fluid inlet port in the housing in flow communication with a particle analyzer for providing particle identification data, a third fluid inlet port in the housing in flow communication with an optical particle counting device for providing particle count data, a syringe degassing port attached to the housing for inverting and degassing a syringe containing a lubricant sample for particle count analysis before injecting the lubricant sample into the third fluid inlet port, an automatic sample injection device for injecting a lubricant sample through the third fluid inlet port, and a microprocessor contained within the housing for collection and manipulation of data from the chemical analysis device, the particle analyzer and the particle counting device;

collecting a lubricant sample to be analyzed;

injecting a first portion of the sample in the first fluid inlet port;

depositing a second portion of the sample in the second fluid inlet port;

degassing a third portion of the sample and injecting the sample into the third fluid inlet port;

collecting and analyzing the chemical analysis data, particle identification data and particle count data; and providing an output to a user indicating corrective action to be taken based on the data.

14. The method of claim 13 wherein the lubricant analysis device contains a sample weighing device for input of lubricant sample weight to the computing device further comprising weighing a lubricant sample to be analyzed.

15. The method of claim 13 wherein the lubricant analysis device includes a vacuum pump in flow communication with the syringe degassing port, further comprising degassing a syringe containing a lubricant sample, inverting the syringe and injecting the lubricant sample into the third fluid inlet port of the lubricant analysis device.

16. The method of claim 15 further comprising diluting the lubricant sample with a solvent prior to degassing the sample.

17. The method of claim 13 wherein the particle analyzer comprises a dual coil electromagnetic sensor, further comprising sequentially imposing first and second magnetic fields on the second sample portion.

18. The method of claim 13 wherein the particle analyzer comprises a permanent magnet wand and a wand holder attached to the housing, further comprising collecting magnetic metal particles on the wand in the second fluid inlet port and removing the wand from the second sample portion.

19. The method of claim 17 wherein the particle analyzer comprises a dual coil electromagnetic sensor, further comprising sequentially imposing first and second magnetic fields on the second sample portion after removing the wand from the second sample portion.

20. The method of claim 13 further comprising diluting the lubricant sample prior to depositing the second portion of the sample in the second fluid inlet port.

21. A lubricant analyzer apparatus comprising a fluid inlet port for a lubricant sample, a sample syringe containing a plunger for injecting the lubricant sample into the fluid inlet port and a syringe degassing device for removing entrained and dissolved gases from the lubricant sample prior to injecting the sample into the inlet port, the degassing device containing a syringe adapter for connecting the syringe in an inverted orientation thereto for degassing a fluid sample in the syringe, a linear motion-controlled arm for attachment to the syringe plunger for injecting the fluid sample into the fluid inlet port at a predetermined rate and a particle counting device in flow communication with the fluid inlet port for providing particle count data respective of particle contamination of the lubricant sample.

22. The lubricant analyzer apparatus of claim 21 further comprising a vacuum pump in flow communication with the degassing device.

23. The lubricant analyzer apparatus of claim 21 wherein the particle counting device is selected from the group consisting of light obscuration devices, light scattering devices and pore blockage devices.

24. The lubricant analyzer apparatus of claim 23 wherein the light scattering device is a laser type photosensor.

* * * * *